United States Patent [19]

Miyaki et al.

[11] 4,246,400
[45] Jan. 20, 1981

[54] TALLYSOMYCIN COMPOUNDS

[75] Inventors: Takeo Miyaki; Osamu Tenmyo; Masataka Konishi, all of Yokohama; Hiroshi Kawaguchi, Tokyo, all of Japan

[73] Assignee: Bristol-Myers Company, New York, N.Y.

[21] Appl. No.: 57,528

[22] Filed: Jul. 13, 1979

[51] Int. Cl.$^3$ ...................... A61K 31/71; C07H 15/22
[52] U.S. Cl. ................................... 536/17 R; 435/77; 424/181
[58] Field of Search ..................................... 536/17 R

[56] References Cited

U.S. PATENT DOCUMENTS

| | | | |
|---|---|---|---|
| 3,681,491 | 8/1972 | Umezawa et al. | 424/115 |
| 3,846,400 | 11/1974 | Umezawa et al. | 260/112.5 R |
| 3,984,390 | 10/1976 | Umezawa et al. | 260/112.5 R |
| 4,051,237 | 9/1977 | Kawaguchi et al. | 424/117 |

FOREIGN PATENT DOCUMENTS

| | | | |
|---|---|---|---|
| 1277150 | 6/1972 | United Kingdom | 424/180 |
| 2001962 | 2/1979 | United Kingdom | 424/180 |

OTHER PUBLICATIONS

Maeda et al., "Jour. Antibiotics", vol. IX, No. 2, Mar. 1956, pp. 82–85.
Umezawa et al., "Jour. Antibiotics", vol. XIX, No. 5, Sep. 1966, pp. 200–209.
Takita et al., "Jour. Antibiotics", vol. XII, No. 3, 1959, p. 111.
Takita "Jour. Antibiotics", vol. XII, No. 6, Nov. 1959, pp. 285–289.
Ikekawa et al., "Jour. Antibiotics", vol. XVII, No. 5, Sep. 1964, pp. 194–199.
Argoudelis et al., "Jour. Antibiotics", vol. XXIV, No. 8, Aug. 1971, pp. 543–557.
Ito et al., "Jour. Antibiotics", vol. XXIV, No. 10, Oct. 1971, pp. 727–731.
Ito et al. "Jour. Antibiotics", vol. XXVI, No. 2, Feb. 1973, pp. 77–83.
Kawamoto et al., "Jour. Antibiotics", vol. XXVIII, No. 5, May 1975, pp. 358–371.
Konishi et al., "Jour. Antibiotics", vol. XXX, No. 10, Oct. 1977, pp. 789–805.
Imanishi et al., "Jour. Antibiotics", vol. XXXI, No. 7, Jul. 1978, pp. 667–674.
Takita et al., "Jour. Antibiotics", vol. XXXI, No. 8, 1978, pp. 801–804.

*Primary Examiner*—Johnnie R. Brown
*Attorney, Agent, or Firm*—David M. Morse

[57] ABSTRACT

Addition of certain amine precursor compounds to the culture medium during fermentation of a tallysomycin-producing strain of *Streptoalloteichus hindustanus* results in production of new tallysomycin derivatives having advantageous antimicrobial and antitumor properties.

23 Claims, No Drawings

TALLYSOMYCIN COMPOUNDS

BACKGROUND OF THE INVENTION

1. Field of the Invention

This invention relates to a novel series of semibiosynthetic tallysomycin derivatives which have advantageous antimicrobial and antitumor properties.

2. Description of the Prior Art

Although a number of glycopeptide antibiotics have been discovered, some of which are also effective in inhibiting the growth of tumors in mammals. there remains a need for additional antimicrobial and antitumor agents. Especially needed are antitumor agents which exhibit increased activity and/or broader spectrum relative to presently available agents or which show fewer undesirable side effects. A brief summary of the more important glycopeptide antibiotics is provided below.

The bleomycins are water-soluble basic glycopeptides produced by fermentation of *Streptomyces verticillus*. They were first reported by Umezawa et al. in *J. Antibiotics* 19A:200 (1966); see also U.S. Pat. No. 3,681,491. The bleomycin complex has been separated into several components including bleomycin $A_1$, $A_2$, $A_5$ and $B_2$. Bleomycin complex is presently being marketed for treatment of various neoplasms in man including squamous cell carcinoma, lymphosarcoma, reticulum cell sarcoma, testicular carcinoma and Hodgkin's disease. A revised structure for the bleomycins has recently been published by H. Umezawa et al. in *J. Antibiotics* 31:801-804 (1978).

The phleomycin group of antibiotics obtained from fermentation of another strain of *Streptomyces verticillus* has been reported by Maeda et al. in *J. Antibiotics:* Vol. A9, pp. 82-85 (1956); Vol. A12, p. 111 (1959); Vol. A12, pg. 285-289 (1959) and Vol. A17, pg. 194-199 (1964). As with bleomycin complex, phleomycin has been separated into a number of components which can exist in both a copper-free and a copper-chelated form.

Zorbamycin and its related antibiotics zorbonomycin B and zorbonomycin C are reported in *J. Antibiotics* 24(8): 543-557 (1971) and in U.K. Pat. No. 1,277,150. These antibiotics isolated from fermentations of *Streptomyces bikiniensis* var. zorbonensis are closely related to the bleomycin and phleomycin families.

Another family of phleomycin-bleomycin group antibiotics has been isolated from the culture broth of a variant of *Streptomyces humidus* of given the name YA-56. A description of the YA-56 complex and active components YA-56X and YA-56Y appears in *J. Antibiotics* 24(10): 727-731 (1971) and in *J. Antiobiotics* 26: 77-83 (1973).

The antibiotic complex XK 49 and its main component victomycin (also called XK 49-1-B-2) are reported in *J. Antibiotics* 28: 358-371 (1975). Victomycin is isolated from a sporangi-forming actinomycete, *Streptosporangium violaceochromogens* MK 49, and appears to be similar to the bleomycins and zorbonomycin B.

The glycopeptide antibiotic complex Bu-2231 and its components Bu-2231 A and B [hereinfter referred to as tallysomycin and tallysomycin A and B, respectively) are disclosed in U.S. Pat. No. 4,051,237; see also *J. Antibiotics:* Vol. 30, pg. 779-805 (1977) and Vol. 31, pg. 667-674 (1978)]. The tallysomycins are isolated from the fermentation broth of certain *Streptoalloteichus hindustanus* strains and exhibit potent antimicrobial and antitumor activities.

Preparation of various semibiosynthetic derivatives of phleomycin and bleomycin by the technique of precursor-fed fermentation has been disclosed in U.S. Pat. Nos. 3,984,390 and 3,846,400. In this procedure strains of microorganisms capable of producing the phleomycin or bleomycin antibiotics are cultured in a fermentation medium in the presence of an amine precursor to produce new phleomycin or bleomycin derivatives having a side chain structure corresponding to the added amine.

U.K. Published Application No. 2,001,962 A discloses preparation of 3-[(S)-1'-phenylethylamino]-propylaminobleomycin (pepleomycin) as an especially preferred semibiosynthetic bleomycin derivative because of its combination of potent antitumor activity and low pulmonary toxicity.

SUMMARY OF THE INVENTION

The present invention provides new semibiosynthetic derivatives of tallysomycin A and B and a process for their preparation. More specifically, there are provided tallysomycin A derivatives of the formula

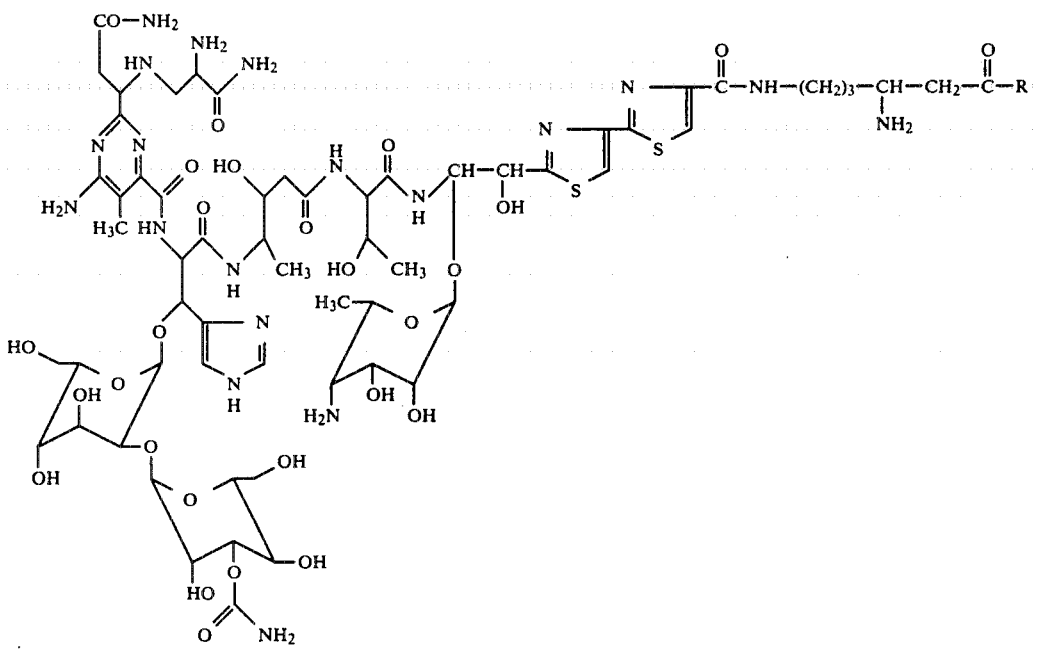
wherein
R is:
—NH—(CH$_2$)$_3$—NH$_2$
—NH—(CH$_2$)$_3$—S⊕(CH$_3$)$_2$
—NH—(CH$_2$)$_3$—NH—CH$_2$CH$_2$OH
—NH—(CH$_2$)$_3$—N(CH$_2$CH$_2$OH)$_2$
—NH—(CH$_2$)$_4$—NH$_2$
—NH—(CH$_2$)$_3$—NH—CH$_3$ or
—NH—(CH$_2$)$_3$—NH—CH(CH$_3$)—C$_6$H$_5$,
and tallysomycin B derivatives of the formula
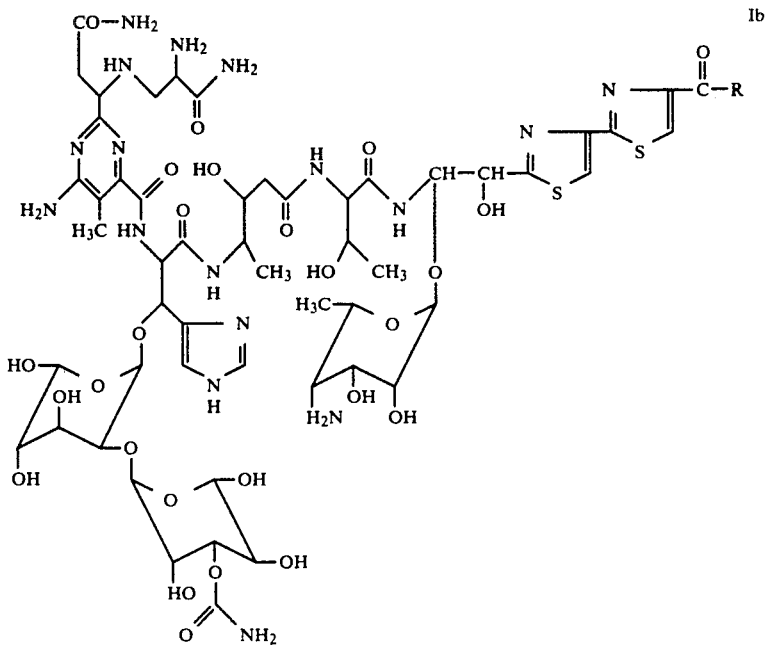
wherein
R is:
—NH—(CH$_2$)$_3$—NH$_2$
—NH—(CH$_2$)$_3$—S⊕(CH$_3$)$_2$
—NH—(CH$_2$)$_2$—NH$_2$

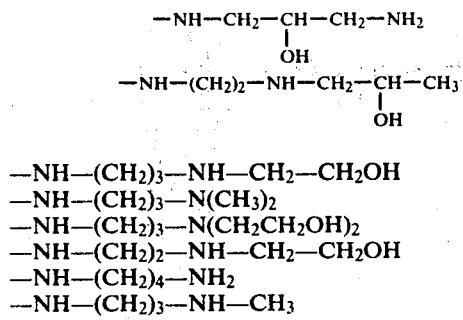

—NH—(CH$_2$)$_3$—NH—CH$_2$—CH$_2$OH
—NH—(CH$_2$)$_3$—N(CH$_3$)$_2$
—NH—(CH$_2$)$_3$—N(CH$_2$CH$_2$OH)$_2$
—NH—(CH$_2$)$_2$—NH—CH$_2$—CH$_2$OH
—NH—(CH$_2$)$_4$—NH$_2$
—NH—(CH$_2$)$_3$—NH—CH$_3$

-continued

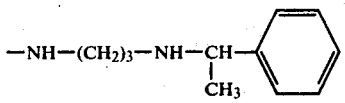

as well as pharmaceutically acceptable acid addition salts of such derivatives. The above-mentioned compounds may exist in the form of a copper chelate or in the copper-free form.

An especially preferred embodiment of the present invention is the tallysomycin B derivative having the formula

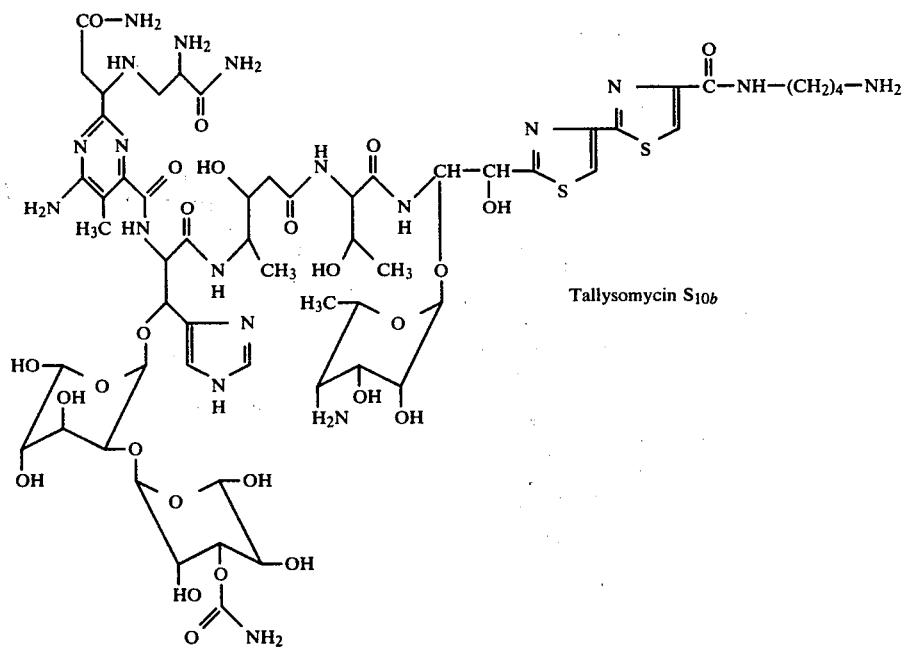

Tallysomycin S$_{10b}$

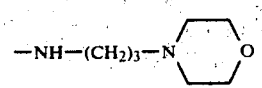

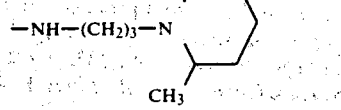

Initial studies using experimental animals indicate that tallysomycin S$_{10b}$ (including both copper-free and copper-chelated forms and pharmaceutically acceptable salts thereof) has excellent antitumor activity against a broad spectrum of malignant tumors and at the same time shows less undesirable side effects (e.g. nephrotoxicity) than the naturally-occurring tallysomycin A and B.

DETAILED DESCRIPTION

U.S. Pat. No. 4,051,237 discloses the production and isolation of two novel glycopeptide antibiotics designated therein as Bu-2231 A and B. Subsequent work has shown that Bu-2231 A and B (now called tallysomycin A and B) have the following structures:

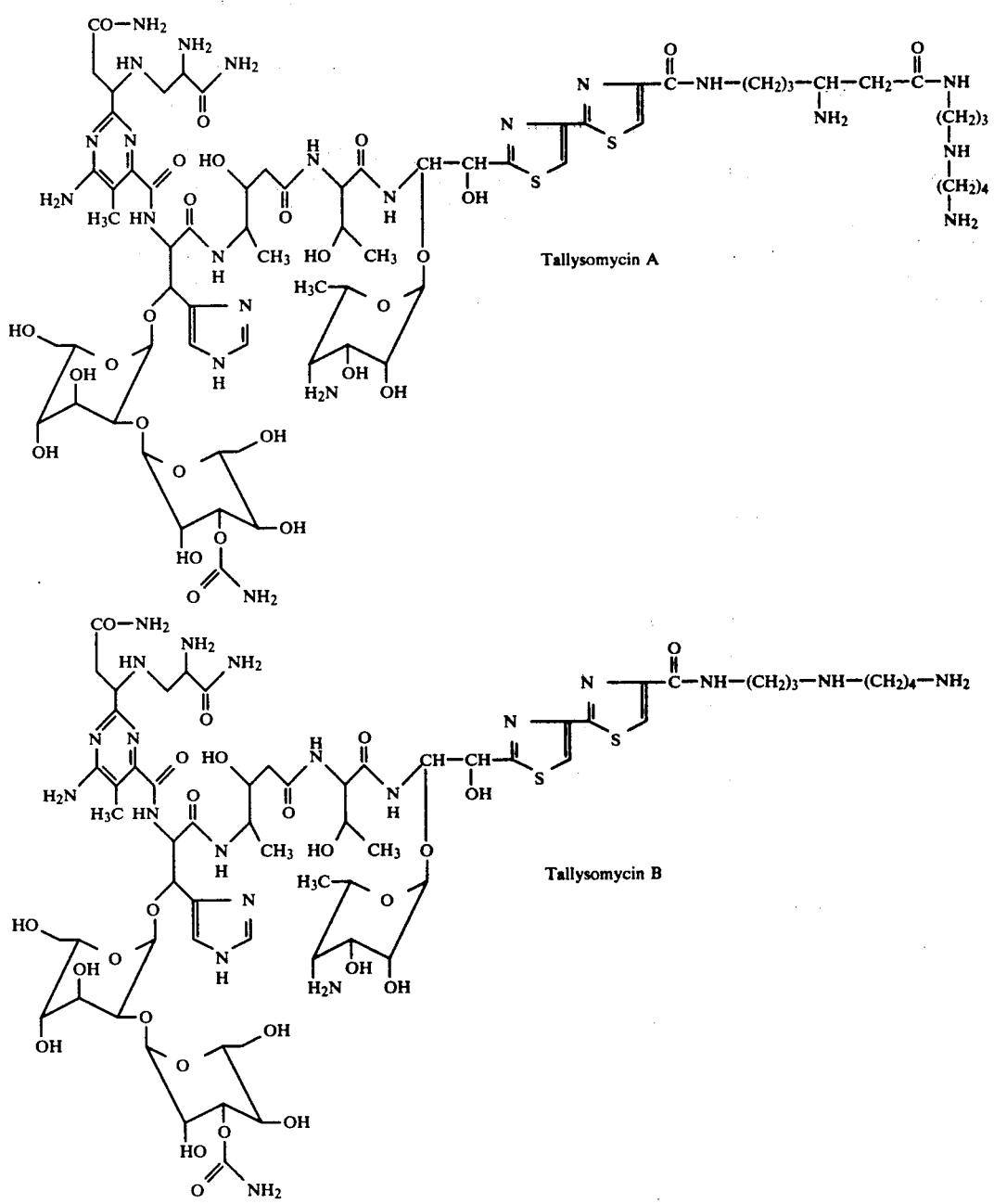

Tallysomycin A

Tallysomycin B

The above-mentioned tallysomycins are the principal components of the fermentation of tallysomycin-producing strains of *Streptoalloteichus hindustanus* and isolation according to conventional chromatographic procedures.

It has now been found according to the present invention that the fermentation procedure disclosed in U.S. Pat. No. 4,051,237 can be carried out in the presence of certain precursor amine compounds to produce new derivatives of tallysomycin A and B having valuable antimicrobial and antitumor properties.

The general technique of precursor amine-fed fermentation described in U.S. Pat. Nos. 3,984,390 and 3,846,400 is utilized in the process of the present invention. In the present process a precursor amine compound is added to the tallysomycin fermentation medium of U.S. Pat. No. 4,051,237 and is incorporated during fermentation into the terminal amine moiety of tallysoymcin A and/or B to form new semibiosynthetic derivatives having a terminal amine side chain corresponding to the added precursor amine. Isolation and purification of the so-obtained derivatives may be carried out by conventional chromatographic procedures such as described in U.S. Pat. No. 4,051,237. A more extensive description of the process is given below and in the illustrative examples which follow.

Preparation of the Antibiotics

In practicing the present process, a tallysomycin-producing strain of *Streptoalloteichus hindustanus* (as disclosed in U.S. Pat. No. 4,051,237), most preferably the strain *Streptoalloteichus hindustanus* E 465-94, ATCC 31158 or a mutant thereof, is cultivated in an aqueous nutrient medium. The nutrient medium contains an assimilable carbon source (e.g. glucose, ribose, galactose, fructose, mannose, sucrose, lactose, soluble starch or glycerol) and an assimilable nitrogen source (e.g. fish meal, soybean meal, cottonseed meal, corn steep liquor, peptones, meat extract, peanut flour, yeast extract or ammonium salts). Inorganic salts such as sodium chloride, potassium chloride, magnesium sulfate, calcium carbonate, phosphates, etc. are added if necessary. Trace elements such as copper, manganese, iron, zinc, etc. are added to the medium if desired or may be supplied as impurities of other media constituents.

In addition to the conventional nutrient constituents described above, there is added to the medium a precursor amine compound as defined below in the form of the free base or as an acid addition salt thereof. Generally, the precursor-amine compound is used in the form of a neutralized aqueous solution. The precursor amine compounds suitable for use in the present invention are listed below along with the codename of the corresponding tallysomycin product:

Fermentation is carried out following the procedure of U.S. Pat. No. 4,051,237. Accordingly, the incubation temperature may be any temperature at which a tallysomycin-producing strain is able to grow, e.g. 20°–54° C., but it is preferable to conduct the fermentation at 25°–35° C., most preferably at 27°–32° C. A neutral or near neutral initial pH, e.g. pH ~ 6-7, is preferably employed in the medium, and production of antibiotic is generally carried out for a period of about 2–10 days. Ordinarily, optimum production is obtained in 3–7 days. For preparation of relatively small amounts, shake flasks and surface culture can be employed, but for large scale production submerged aerobic culture in sterile tanks is preferred. When tank fermentation is to be carried out, it is desirable to produce a vegetative inoculum in a nutrient broth by inoculating the broth culture with a spore from the producing organism. When a young active vegetative inoculum has been obtained, the inoculum is transferred aseptically to the fermentation tank medium. Aeration in tanks and bottles may be provided by forcing air through or onto the surface of the fermenting medium. Agitation in tanks may be pro-

| Chemical Name | Amine Structure | Tallysomycin End Product* |
|---|---|---|
| 1,2-diaminoethane | $NH_2-(CH_2)_2-NH_2$ | $S_{3b}$ |
| 1,3-diaminopropane | $NH_2-(CH_2)_3-NH_2$ | $S_{1a}, S_{1b}$ |
| 1,4-diaminobutane | $NH_2-(CH_2)_4-NH_2$ | $S_{10a}, S_{10b}$ |
| 1,3-diamino-2-hydroxy-propane | $NH_2-CH_2-\underset{\underset{OH}{\mid}}{CH}-CH_2-NH_2$ | $S_{4b}$ |
| N-(β-hydroxyethyl)-1,2-diaminoethane | $NH_2-(CH_2)_2-NH-CH_2-CH_2OH$ | $S_{9b}$ |
| N-(β-hydroxypropyl)-1,2-diaminoethane | $NH_2-(CH_2)_2-NH-CH_2-\underset{\underset{OH}{\mid}}{CH}-CH_3$ | $S_{5b}$ |
| N-methyl-1,3-diaminopropane | $NH_2-(CH_2)_3-NH-CH_3$ | $S_{11a}, S_{11b}$ |
| N-(β-hydroxyethyl)-1,3-diaminopropane | $NH_2-(CH_2)_3-NH-CH_2-CH_2OH$ | $S_{6a}, S_{6b}$ |
| N-(1'-phenylethyl)-1,3-diaminopropane | 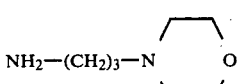 | $S_{14a}, S_{14b}$ |
| N,N-dimethyl-1,3-diaminopropane | $NH_2-(CH_2)_3-N(CH_3)_2$ | $S_{7b}$ |
| N,N-di(β-hydroxyethyl)-1,3-diaminopropane | $NH_2-(CH_2)_3-N(CH_2-CH_2OH)_2$ | $S_{8a}, S_{8b}$ |
| N-(3-aminopropyl)-morpholine | $NH_2-(CH_2)_3-N\underset{}{\overset{}{\diagup\diagdown}}O$ | $S_{12b}$ |
| N-(3-aminopropyl)-2-pipecoline | 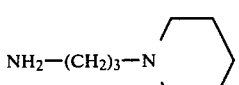 | $S_{13b}$ |
| 3-aminopropyl-dimethyl-sulfonium chloride | $NH_2-(CH_2)_3-\underset{\underset{Cl^{\ominus}}{\mid}}{S^{\oplus}}(CH_3)_2$ | $S_{2a}, S_{2b}$ |

*The tallysomycin derivatives are named by assigning each precursor amine a number and then designating the tallysomycin end-product by the number of its terminal amine and the letter a or b depending on whether it is a derivative of tallysomycin A or B. For example tallysomycin $S_{10b}$ is the tallysomycin B derivative having 1,4-diaminobutane as the terminal amine.

The amines, utilized as free base compounds or as acid addition salts with mineral acids such as HBr or HCl, are preferably added to the medium at a concentration of about 0.05 to 0.4% (w/v), more preferably about 0.1 to 0.2% (w/v), at the beginning of fermentation, although good results can also be achieved by portionwise addition of amine solution during the early stages of fermentation.

vided by a mechanical impeller, and an antifoaming agent such as lard oil may be added as needed.

Production of the desired tallysomycin derivative in the culture medium can be followed during the course of the fermentation by the paper disc-agar diffusion method using Mycobacterium smegmatis strain M6-3 as the test organism.

Isolation and Purification

After optimum broth potency has been obtained (as determined, for example, by the assay procedure mentioned above), the mycelium and undissolved residues are separated from the fermentation broth by conventional means such as filtration or centrifugation. The antibiotic activity is in the filtrate and can be recovered therefrom by employing conventional adsorption techniques; see, for example, J. Antibiotics 30(10): 779-788 (1977).

In a preferred embodiment the filtrate is first adsorbed on a cationic exchange resin, for example a resin of the type available from Rohm & Haas Company under the tradename AMBERLITE IRC-50 ($NH_4^+$ form). The resin is washed with water and the tallysomycin fractions eluted with aqueous mineral acid, e.g. 0.1 N HCl. The eluate containing the active fractions is neutralized with aqueous ammonia and preferably stirred with activated carbon. The charcoal is collected by filtration, washed with water and then eluted with aqueous butanol (1:1 butanol:dil. HCl v/v) at acid pH (e.g. pH 2). The aqueous layer of eluant is neutralized with a basic anion exchange resin and concentrated in vacuo. Concentrated eluate from the IRC-50 (if the carbon adsorption step is omitted) or activated carbon is next dissolved in water, adsorbed on a resin of the DIAION HP-20 (tradename for a macroporous, non-ionic adsorbent resin composed of a styrene-divinylbenzene copolymer available from Mitsubishi Chemical Co., Japan) type and eluted with water to give a mixture of crude tallysomycins in the copper chelate form.

Separation and purification of the desired tallysomycin derivatives formed during the precursor-fed fermentation may be achieved by adsorbing the crude tallysomycin complex obtained above on a modified dextran derivative cationic ion exchanger, for example a modified polysaccharide dextran of the type sold commercially under the tradename CM-SEPHADEX C-25 by Pharmacia Fine Chemicals Inc. The tallysomycin derivative(s) is eluted in a stepwise manner with aqueous ammonium formate solution of concentrations varying from about 1-7%. Fractions containing the same derivative are pooled, desalted by activated carbon adsorption (elution with acidic aqueous butanol) and lyophilized to give purified tallysomycin derivative as a copper chelate. Further purification can be achieved if desired by conventional chromatographic and/or gel filtration techniques.

The tallysomycin derivatives of the present invention have the property of chelating with copper as do tallysomycin A and B and thus the new derivatives and their acid addition salts may exist in the copper-complex form or copper-free form. The copper-free forms of the tallysomycin derivatives may be prepared from the corresponding copper-complex forms by known procedures such as those disclosed in U.S. Pat. No. 4,051,237 and U.K. Published Application No. 2,001,962 A.

The tallysomycin free base derivatives of the present invention may be converted by conventional methods to pharmaceutically acceptable acid addition salts. Examples of such salts include the non-toxic salts with organic or inorganic acids such as hydrochloric, sulfuric, phosphoric acetic, formic, stearic, maleic, benzoic, succinic and hydrobromic.

Antimicrobial Activity

The minimum inhibitory concentrations (MIC) of the semibiosynthetic tallysomycin derivatives of the present invention were determined against fungi and gram-positive, gram-negative and acid-fast bacteria by the two-fold agar dilution method. Nutrient agar was used for bacteria and Sabouraud agar for fungi. The results are shown in the table below comparatively with tallysomycin A and B.

| Antimicrobial Activity of Tallysomycin Derivatives | | | | |
|---|---|---|---|---|
| Tallyso-mycin | Staphylo-coccus aureus Smith | Sacrcina lutea PCI1001 | Bacillus subtilis PCI 219 | Myco-bacterium 607 |
| A | 0.1 | 0.05 | <0.003 | 0.2 |
| B | 0.4 | 0.4 | 0.006 | 0.2 |
| $S_{1a}$ | 0.4 | 0.1 | <0.003 | 0.012 |
| $S_{1b}$ | 1.6 | 1.6 | <0.05 | <0.05 |
| $S_{2a}$ | 0.2 | 0.8 | <0.05 | <0.05 |
| $S_{2b}$ | 1.6 | 6.3 | <0.05 | 0.2 |
| $S_{3b}$ | 0.8 | 1.6 | 0.013 | 0.05 |
| $S_{4b}$ | 0.8 | 3.1 | 0.006 | 0.003 |
| $S_{5b}$ | 6.3 | 12.5 | 0.025 | 0.2 |
| $S_{6a}$ | 0.8 | 1.6 | 0.03 | 0.4 |
| $S_{6b}$ | 6.3 | 12.5 | 0.02 | 0.2 |
| $S_{7b}$ | 6.3 | 12.5 | 0.1 | 3.1 |
| $S_{8a}$ | 0.2 | 0.4 | 0.006 | 0.1 |
| $S_{8b}$ | 0.4 | 0.8 | 0.013 | 0.1 |
| $S_{9b}$ | 0.4 | 0.8 | 0.013 | 0.1 |
| $S_{10a}$ | 1.6 | 0.4 | 0.04 | 0.2 |
| $S_{10b}$ | 6.3 | 3.1 | 0.2 | 0.2 |
| $S_{11a}$ | 0.8 | 0.2 | 0.025 | 0.1 |
| $S_{11b}$ | 3.1 | 0.8 | 0.1 | 0.1 |
| $S_{12b}$ | 12.5 | 12.5 | 0.4 | 0.2 |
| $S_{13b}$ | 6.3 | 6.3 | 0.8 | 0.2 |
| $S_{14a}$ | 0.8 | 0.8 | 0.1 | 0.1 |
| $S_{14b}$ | 3.1 | 3.1 | 0.4 | 0.2 |
| Tallyso-mycin | Escherichia coli NIHJ | Proteus mirabilis A9554 | Candida albicans IAM 4888 | Aspergillus fumigatus IAM 2593 |
| A | 0.05 | 0.4 | 12.5 | 1.6 |
| B | 0.2 | 0.2 | 6.3 | 0.8 |
| $S_{1a}$ | 0.1 | 0.4 | 3.1 | 0.8 |
| $S_{1b}$ | 0.4 | 1.6 | 12.5 | 1.6 |
| $S_{2a}$ | <0.05 | 0.2 | 6.3 | 0.4 |
| $S_{2b}$ | 0.4 | 1.6 | 25 | 0.8 |
| $S_{3b}$ | 0.1 | 0.2 | 12.5 | 0.8 |
| $S_{4b}$ | 0.4 | 0.4 | 25 | 0.8 |
| $S_{5b}$ | 0.4 | 3.1 | 25 | 0.4 |
| $S_{6a}$ | 0.4 | 1.6 | 6.3 | 0.2 |
| $S_{6b}$ | 0.4 | 3.1 | 25 | 0.8 |
| $S_{7b}$ | 0.4 | 6.3 | >50 | 0.4 |
| $S_{8a}$ | 0.1 | 0.4 | 12.5 | 0.8 |
| $S_{8b}$ | 0.2 | 0.8 | >50 | 1.6 |
| $S_{9b}$ | 0.1 | 0.8 | 25 | 1.6 |
| $S_{10a}$ | 0.4 | 0.8 | 3.1 | 1.6 |
| $S_{10b}$ | 0.8 | 3.1 | 12.5 | 6.3 |
| $S_{11a}$ | 0.1 | 0.2 | 1.6 | 0.8 |
| $S_{11b}$ | 0.2 | 1.6 | 12.5 | 6.3 |
| $S_{12b}$ | 1.6 | 50 | >100 | 25 |
| $S_{13b}$ | 0.4 | 12.5 | >100 | 12.5 |
| $S_{14a}$ | 0.2 | 3.1 | 50 | 3.1 |
| $S_{14b}$ | 0.4 | 25 | >100 | 25 |

The relative antibacterial potencies (tallysomycin A standard = 1000 mcg/mg) of the tallysomycin derivatives were determined by the paper-disc agar diffusion method using *Mycobacterium smegmatis* strain M6-3 as the assay organism. The results are shown in the following table.

| Antibacterial Potency of Tallysomycin Derivatives | |
|---|---|
| Tallysomycin | Antibacterial potency (μ/mg) |
| A | 1,000 |
| B | 900 |
| $S_{1a}$ | 1,075 |
| $S_{1b}$ | 1,000 |
| $S_{2a}$ | 350 |
| $S_{2b}$ | 300 |
| $S_{3b}$ | 725 |
| $S_{4b}$ | 405 |
| $S_{5b}$ | 500 |
| $S_{6a}$ | 460 |
| $S_{6b}$ | 340 |
| $S_{7b}$ | 380 |
| $S_{8a}$ | 550 |
| $S_{8b}$ | 370 |
| $S_{9b}$ | 380 |
| $S_{10a}$ | 1,450 |
| $S_{10b}$ | 1,100 |
| $S_{11a}$ | 570 |
| $S_{11b}$ | 450 |
| $S_{12b}$ | 390 |
| $S_{13b}$ | 1,090 |
| $S_{14a}$ | 1,300 |
| $S_{14b}$ | 1,090 |

Antitumor Activity

The activity of prophage induction of lysogenic bacterium *E. coli* W1709 (λ) was determined according to the method disclosed by Lein et al. in *Nature* 196: 783–784 (1962). The plaque count was made on the agar plate containing test compound (t) and control plate (c). A t/c ratio of the plaque counts of greater than 3.0 was defined to be a significant level and lysogenic induction activity (ILB activity) was expressed by the minimum inducible concentration of the test compound. Results are given in the following table.

| ILB Activity of Tallysomycin Derivatives | |
|---|---|
| Tallysomycin | ILB activity (mcg/ml) |
| A | 0.00125 |
| B | 0.01 |
| $S_{1a}$ | 0.16 |
| $S_{1b}$ | 0.31 |
| $S_{2a}$ | 0.31 |
| $S_{2b}$ | 0.63 |
| $S_{3b}$ | 0.31 |
| $S_{4b}$ | — |
| $S_{5b}$ | 0.08 |
| $S_{6a}$ | 0.02 |
| $S_{6b}$ | 0.08 |
| $S_{7b}$ | 0.08 |
| $S_{8a}$ | 0.005 |
| $S_{8b}$ | 0.02 |
| $S_{9b}$ | 0.16 |
| $S_{10a}$ | 0.16 |
| $S_{10b}$ | 0.31 |
| $S_{11a}$ | 0.08 |
| $S_{11b}$ | 0.63 |
| $S_{12b}$ | 0.31 |
| $S_{13b}$ | 0.08 |
| $S_{14a}$ | 0.01 |
| $S_{14b}$ | 0.04 |

The antitumor activity of the tallysomycin derivatives was examined in four experimental tumor systems in mice. Lymphocytic leukemia P388 and Lewis lung carcinoma were implanted intraperitoneally into $BDF_1$ mice of either sex at an inoculum size of $3 \times 10^5$ and $5 \times 10^5$ cells per mouse, respectively. Sarcoma 180 ascites tumor was inoculated intraperitoneally into male dd-strain mice with $2.5 \times 10^{16}$ cells per mouse. Melanotic melanoma B16 was implanted subcutaneously into $BDF_1$ mice with $5 \times 10^5$ cells per mouse. Twenty-four hours after the implantation of tumor cells, graded doses of test compounds were administered to mice intraperitoneally in an injection volume of 0.2 ml. per 10 grams of body weight. Test compounds were given once daily for 9 days (qd 1→9 schedule) except for the mice inoculated with Lewis lung carcinoma which were treated for 11 days (qd 1→11). Death or survival of the treated and non-treated (control) animals was recorded daily during the observation period of 45 days after the implantation of tumor cells, and the median survival time was calculated for each of the test (T) and control (C) groups. A T/C value equal to or greater than 125% indicates that a significant antitumor effect was achieved against leukemia P388 and Lewis lung carcinoma. The actual dose giving a T/C of 125% was estimated by linear regression analysis and defined as the effective dose 125 or $ED_{125}$. The effective dose 150 ($ED_{150}$) was employed for the evaluation of antitumor effect against Sarcoma 180. In the B16 melanoma experiment the tumor size was measured on day 16 after tumor inoculation, and the dose giving 50% inhibition of tumor growth ($ID_{50}$) was calculated from regression lines. Antitumor activity of the derivatives is set forth in the following table.

| | Antitumor activity (mg/kg/day, ip) | | | |
|---|---|---|---|---|
| Tallsomycin* | P388 ($ED_{125}$) | S180 $ED_{150}$ | B16 ($ID_{50}$) | Lewis lung $ED_{125}$ |
| A (Cu-free) | 0.26 | 0.07 | 0.27 | 0.13 |
| B (Cu-free) | 0.89 | 0.06 | 0.82 | 0.11 |
| $S_{1a}$ | 1.2 | 0.07 | 0.84 | — |
| $S_{1b}$ | 2.0 | 0.11 | 0.15 | 0.12 |
| $S_{2a}$ | >3.0 | 0.07 | 0.17 | 0.14 |
| $S_{2b}$ | 0.91 | 0.12 | 0.33 | 0.65 |
| $S_{3b}$ | 0.32 | 0.06 | 0.20 | 0.26 |
| $S_{4b}$ | >3.0 | 0.13 | 0.50 | — |
| $S_{5b}$ | 0.66 | 0.10 | 0.31 | 0.38 |
| $S_{6a}$ | 0.70 | 0.09 | 0.12 | 0.47 |
| $S_{6b}$ | 2.2 | 0.08 | 0.22 | 0.17 |
| $S_{7b}$ | 2.1 | 0.14 | 0.16 | — |
| $S_{8a}$ | 0.78 | — | — | — |
| $S_{8b}$ | 1.5 | 0.25 | 0.26 | 0.12 |
| $S_{9b}$ | >3.0 | 0.42 | 0.29 | 0.41 |
| $S_{10a}$ | 0.28 | 0.08 | 0.39 | — |
| $S_{10b}$ | — | 0.03 | 0.59 | — |
| $S_{10b}$ (Cu-free) | 0.47 | 0.02 | 0.75 | 0.21 |
| $S_{11a}$ | 0.60 | — | — | — |
| $S_{11b}$ | 0.28 | 0.20 | 0.70 | 0.32 |
| $S_{12b}$ | 1.30 | 0.06 | 1.30 | — |
| $S_{13b}$ | 0.70 | 0.33 | 0.23 | — |
| $S_{14a}$ | — | — | — | — |
| $S_{14b}$ | 3.0 | 0.08 | 0.43 | 0.29 |

*copper-chelated form unless otherwise stated

Graded doses of test compounds were administered intraperitoneally to groups of dd mice. The injection was given one time only or once daily for 9 consecutive days. Death or survival of the animals was recorded for 30 days after the last dose of test compound to calculate the single or multiple median lethal dose ($LD_{50}$). Results are shown below.

| Acute and Subacute Toxicity of Tallysomycin Derivatives | | |
|---|---|---|
| | $LD_{50}$ (mg/kg/day, ip) | |
| Tallysomycin* | single dose | multiple dose (qd 1 → 9) |
| A (Cu-free) | 19 | 4.4 |
| B (Cu-free) | 46 | 6.8 |
| $S_{1a}$ | 25 | — |

-continued

Acute and Subacute Toxicity of Tallysomycin Derivatives

| Tallysomycin* | LD$_{50}$ (mg/kg/day, ip) | |
|---|---|---|
| | single dose | multiple dose (qd 1 → 9) |
| S$_{1b}$ | 19 | — |
| S$_{2a}$ | 25 | — |
| S$_{2b}$ | 32 | 2.0 |
| S$_{3b}$ | 19 | — |
| S$_{4b}$ | 13 | — |
| S$_{5b}$ | 46 | 4.0 |
| S$_{6a}$ | 15 | — |
| S$_{6b}$ | 30 | — |
| S$_{7b}$ | 30 | — |
| S$_{8a}$ | 42 | — |
| S$_{8b}$ | 30 | — |
| S$_{9b}$ | 32 | — |
| S$_{10a}$ | 27 | — |
| S$_{10b}$ | 27 | — |
| S$_{10b}$ (Cu-free) | 42 | 4.0 |
| S$_{11a}$ | 18 | — |
| S$_{11b}$ | 21 | — |
| S$_{12b}$ | >50 | — |
| S$_{13b}$ | 35 | — |
| S$_{14a}$ | — | — |
| S$_{14b}$ | — | 16 |

*copper-chelated form unless otherwise stated

The antitumor therapeutic index was calculated for each derivative from the ratio of toxicity and antitumor activity. As shown in the following table, several of the new semibiosynthetic tallysomycin derivatives demonstrated better therapeutic indices than the naturally obtained tallysomycin A and B in some of the experimental tumor systems examined.

Antitumor Therapeutic Indices of Tallysomycin Derivatives

| Tallysomycin* | Antitumor therapeutic indices** | | | |
|---|---|---|---|---|
| | P388 | S180 | B16 | Lewis Lung |
| A (Cu-free) | 73 | 271 | 70 | 146 |
| B (Cu-free) | 52 | 767 | 56 | 418 |
| S$_{1a}$ | 21 | 357 | 30 | — |
| S$_{1b}$ | 10 | 173 | 127 | 158 |
| S$_{2a}$ | <8 | 357 | 147 | 179 |
| S$_{2b}$ | 35 | 267 | 97 | 49 |
| S$_{3b}$ | 59 | 317 | 95 | 73 |
| S$_{4b}$ | <4 | 100 | 26 | — |
| S$_{5b}$ | 70 | 460 | 148 | 121 |
| S$_{6a}$ | 21 | 167 | 125 | 32 |
| S$_{6b}$ | 14 | 375 | 136 | 176 |
| S$_{7b}$ | 14 | 214 | 188 | — |
| S$_{8a}$ | 54 | — | — | — |
| S$_{8b}$ | 20 | 120 | 115 | 250 |
| S$_{9b}$ | <11 | 76 | 110 | 78 |
| S$_{10a}$ | 96 | 338 | 69 | — |
| S$_{10b}$ | — | 900 | 46 | — |
| S$_{10b}$ (Cu-free) | 89 | 2100 | 50 | 200 |
| S$_{11a}$ | 30 | — | — | — |
| S$_{11b}$ | 75 | 105 | 30 | 66 |
| S$_{12b}$ | >38 | >833 | >38 | — |
| S$_{13b}$ | 50 | 106 | 152 | — |
| S$_{14a}$ | — | — | — | — |
| S$_{14b}$ | — | — | — | — |

*copper-chelated form unless otherwise stated
**single dose toxicity (LD$_{50}$)/antitumor effective dose (ED$_{125}$, ED$_{150}$ or ID$_{50}$)

Tallysomycin S$_{10b}$ was evaluated for nephrotoxicity in a mouse model utilizing BUN measurement as an endpoint and a lung hydroxyproline model for pulmonary toxicity (see Cancer Res. 35:787 (1978)). Tallysomycin S$_{10b}$ toxicity to the kidney was no greater than that of bleomycin at equitoxic doses. Tallysomycin S$_{10b}$ caused an increase in lung hydroxyproline suggesting pulmonary toxicity. However, the dose response slope was flatter than that observed with bleomycin and the hydroxyproline content at high doses was reduced compared to that of animals treated with bleomycin at equitoxic doses.

As indicated by the data provided above, the tallysomycin derivatives of the present invention are useful as antimicrobial agents for inhibiting the growth of microbial organisms, both bacteria and fungi, which are pathogenic to animal and plant life. They are also useful in inhibiting the growth of tumors in experimental animals. The compounds may be administered in the same manner as commercially available bleomycin, and optimum dosage levels for a given set of conditions can be ascertained by those skilled in the art using conventional dosage determination tests and the data provided above.

The present invention includes within its scope pharmaceutical compositions which comprise an effective antimicrobial or experimental animal tumor-inhibiting amount of a tallysomycin derivative of the present invention, or a pharmaceutically acceptable acid addition salt thereof, in combination with an inert pharmaceutically acceptable carrier or diluent.

According to another aspect of the invention, a method is provided for therapeutically treating an animal (preferably mammalian) host affected by a microbial infection or an experimental animal host affected by a malignant tumor which comprises administering to such host an effective antimicrobial or tumor-inhibiting dose of a tallysomycin derivative of the present invention or a pharmaceutically acceptable acid addition salt thereof.

The following examples are provided for illustrative purposes only and are not intended to limit the scope of the invention.

EXAMPLE 1

S$_{2a}$ and S$_{2b}$

Malt extract agar slant inoculated with *Streptoalloteichus hindustanus* ATCC 31158 was incubated for a week at 28° C. The slant was used to inoculate 100 ml. of germination medium having the following composition in a 500 ml. Erlenmeyer flask:

glucose—1.5%
yeast extract—0.2
polypeptone—0.5
K$_2$HPO$_4$—0.05
MgSO$_4$.7H$_2$O—0.05
CaCO$_3$—0.5

The pH was adjusted to 7.2 before sterilization in an autoclave. The seed culture flasks were incubated at 33° C. for 48 hours on a rotary shaker operating at 230 rpm. The seed culture obtained above was transferred to 100 ml. of fermentation medium in a 500 ml. Erlenmeyer flask at an inoculum size of 10% (v/v). The fermentation medium contained the following ingredients:

sucrose—2.5%
glucose—0.5
PHARMAMEDIA (cottonseed meal)—3.0
distiller's soluble—3.0
(NH$_4$)$_2$SO$_4$—0.3
ZnSO$_4$.7H$_2$O—0.003
CuSO$_4$.5H$_2$O—0.01
CaCO$_3$—0.4

A neutralized aqueous solution of 3-aminopropyldimethylsulfonium chloride, was added to the fermentation medium before sterilization at a concentration of 0.1% (w/v) as the hydrochloride salt. The pH of the medium was adjusted to 7.0 before sterilization. The inoculated fermentation flasks were incubated at 28° C. for five days on a rotary shaker operating at 250 rpm. The progress of the fermentation was monitored by paper disc-agar diffusion assay using *M. smegmatis* strain M6-3 as the test organism.

The fermentation broth containing tallysomycins $S_{2a}$ and $S_{2b}$ was stirred with filter aid and the filtrate (20 L) was stirred with AMBERLITE IRC-50 (60% $NH_4^+$ form, 3.5 L). The resin was washed with water and then the activity was eluted with 0.2 N HCl (4 L×3). The active eluate was adjusted to pH 6.0 and stirred with activated charcoal (400 g.). Bioactive components adsorbed on the activated carbon were eluted by stirring three times with a mixture of n-butanol and water, the pH being kept at 2.0 during the elution. The combined aqueous eluate was neutralized and concentrated in vacuo to ca. 100 ml and the concentrate chromatographed on a column of DIAION HP-20 (1.2 L). The column was developed with water to collect blue-colored tallysomycin fractions. Evaporation of appropriate fractions gave a crude tallysomycin mixture (4.85 g) which was chromatographed on a column of CM-SEPHADEX C-25 (330 ml) developed with an increasing concentration of ammonium formate solution. Tallysomycin $S_{2b}$, $S_{2a}$ and B were successively eluted with 2% $HCOONH_4$ and tallysomycin A eluted with 4% $HCOONH_4$. Each antibiotic fraction was desalted by activated carbon adsorption followed by elution with acidic aqueous n-butanol. Lyophilization of the aqueous eluate yielded tallysomycin $S_{2a}$ (156 mg) and $S_{2b}$ (570 mg) along with tallysomycin A (210 mg) and B (540 mg), all in a copper-chelated form.

EXAMPLE 2

$S_{6a}$ and $S_{6b}$

The fermentation procedure of Example 1 was repeated except that N-(β-hydroxyethyl)-1,3-diaminopropane (HCl salt) was used as the precursor amine. The harvested broth (11 L) was filtered with filter aid. The antibiotic activity in the filtrate was adsorbed on AMBERLITE IRC-50 resin (60% $NH_4^+$ form, 2.4 L) and eluted from the resin with 0.1 N HCl. The eluate was adjusted to pH 6.5 and then passed through a column of DIAION HP-20 (2 L). The column was eluted with water. Fractions containing tallysomycins were concentrated in vacuo and lyophilized to give blue solid (824 mg). Tallysomycins were separated by CM-SEPHADEX C-25 chromatography (200 ml) using aqueous ammonium formate solution as eluant. Tallysomycin $S_{6b}$ was eluted with 2% $HCOONH_4$, $S_{6a}$ and B with 3% $HCOONH_4$ and finally A with 5% $HCOONH_4$ solution. Each fraction was treated with activated charcoal for desalting. Yields of copper-chelated tallysomycins were: A 61 mg, B 31 mg, $S_{6a}$ 201 mg and $S_{6b}$ 288 mg.

EXAMPLE 3

$S_{8a}$ and $S_{8b}$

The fermentation procedure of Example 1 was repeated except that N,N-di(β-hydroxyethyl)-1,3-diaminopropane (HCl salt) was used as the precursor amine in a concentration of 0.2% (w/v). The harvested broth (10 L) was filtered. Tallysomycin components in the culture filtrate were adsorbed by AMBERLITE IRC-50 (60% $NH_4^+$ form, 2.2 L) and eluted with dilute HCl solution. The active eluate was neutralized and applied on a column of DIAION HP-20 (2 L) which was developed with water. The bioactive fractions were concentrated in vacuo to afford 1.16 g of crude tallysomycins. The solid was chromatographed on a column of CM-SEPHADEX C-25 (300 ml). Tallysomycin $S_{8b}$ was eluted first from the column with 2% $HCOONH_4$, $S_{8a}$ and B with 3% $HCOONH_4$ and then A with 5% $HCOONH_4$ solution. The appropriate fractions were desalted by carbon adsorption. Yields of copper-chelated tallysomycins were: A 184 mg, B 171 mg, $S_{8a}$ 63 mg and $S_{8b}$ 248 mg.

EXAMPLE 4

$S_{10a}$ and $S_{10b}$

The fermentation procedure of Example 1 was repeated except that 1,4-diaminobutane dihydrochloride was used as the precursor amine compound. The fermentation broth (35 L, pH 7.5) was centrifuged to separate mycelial cake. The clear supernatant thus obtained was stirred with AMBERLITE IRC-50 resin (60% $NH_4^+$ form, 6 L) for 30 minutes. The resin was washed with two 30 L portions of water and then eluted with three 10 L portions of acidic water, the pH being kept below 2.0 during the elution. The eluates were combined, adjusted to pH 7.8 and stirred with activated charcoal (800 g). The activity was eluted with a 1:1 mixture of n-butanol and acidic water (5 L each, pH 2.0) and the elution was repeated three times. The aqueous layers were combined, neutralized with *AMBERLITE IR-45 (OH-form) and concentrated in vacuo to 300 ml. The concentrate was applied on a column of DIAION HP-20 (3 L) which was developed with water. The elution was monitored by bioassay and the bioactive fractions were concentrated to afford a mixture of tallysomycins as a blue solid (6 g). The solid was chromatographed on a column of CM-SEPHADEX C-25 (300 ml) which was pre-washed with 1% $HCOONH_4$ solution. The column was developed with increasing concentrations (1%~3%) of aqueous ammonium formate solution. The first bioactive fractions eluted with 3% $HCOONH_4$ were combined (250 ml) and stirred with 30 g of activated charcoal. The carbon was separated, washed with water and eluted twice with a 1:1 mixture of n-butanol and acidic water (120 ml each). The aqueous eluates were neutralized with AMBERLITE IR-45 (OH-form) resin and then evaporated to give a semi-pure preparation of tallysomycin $S_{10b}$ (1.60 g). The sample was chromatographed again on a column of +Amberlite XT-2 (240 ml) which was developed with water. The bioactive eluates were combined, concentrated and lyophilized to afford pure copper-chelated tallysomycin $S_{10b}$ (1.25 g). Tallysomicin $S_{10a}$ and B were successively eluted out from the CM-SEPHADEX column with 3% $HCOONH_4$ solution to yield copper-chelated tallysomycin $S_{10a}$ (360 mg) and tallysomycin B (370 mg). A trace amount of tallysomycin A was obtained from 5% $HCOONH_4$ eluate.

*basic anion exchange resin available from Rohms & Haas Co., U.S.A.
+macroporous, non-ionic styrene-divinylbenzene copolymer adsorption resin, fine particle grade, available from Rohm & Haas Co., U.S.A.

EXAMPLE 5

By essentially the same procedure as described in Examples 1–4, the following semibiosynthetic tallysomycin derivatives were prepared by amine-fed fermentation.

| Tallyso-mycin Derivative Product | Amine Hydrochloride Precursor Compound | Fermentation Broth Volume (L) | Yield (mg) |
|---|---|---|---|
| $S_{1a}$ | 1,3-diaminopropane | 6.7 | trace |
| $S_{1b}$ | 1,3-diaminopropane | " | 70 |
| $S_{3b}$ | 1,2-diaminoethane | 1.9 | 6 |
| $S_{4b}$ | 1,3-diamino-2-hydroxypropane | 8.5 | 17 |
| $S_{5b}$ | (N-$\beta$-hydroxypropyl)-1,2-diaminoethane | 5 | 32 |
| $S_{7b}$ | N,N-dimethyl-1,3-diaminopropane | 10 | 96 |
| $S_{9b}$ | N-($\beta$-hydroxyethyl)-1,2-diaminoethane | 10 | 286 |
| $S_{11a}$ | N-methyl-1,3-diaminopropane | 3.2 | 43 |
| $S_{11b}$ | N-methyl-1,3-diaminopropane | " | 259 |
| $S_{12b}$ | N-(3-aminopropyl)morpholine | 2.2 | 94 |
| $S_{13b}$ | N-(3-aminopropyl)-2-pipecoline | 10 | 137 |
| $S_{14a}$ | N-(1'-phenylethyl)-1,3-diaminopropane | 4 | 20 |
| $S_{14b}$ | N-(1'-phenylethyl)-1,3-diaminopropane | " | 210 |

EXAMPLE 6

The copper-free tallysomycins corresponding to the copper-chelated derivatives prepared in Examples 1–5 may be obtained by treatment with $H_2S$ in methanol according to the procedure of Example 1 of U.S. Pat. No. 3,646,197.

Physico-chemical properties of the tallysomycin derivatives prepared in Examples 1–5 are shown in the table below.

| Tallysomycin | TLC ($R_f$)** S-102 | TLC ($R_f$)** S-123 | HPLC++ (retention time) |
|---|---|---|---|
| $S_{1a}$ | 0.50 | 0.23 | 6'24" |
| $S_{1b}$ | 0.65 | 0.37 | 4'48" |
| $S_{2a}$ | 0.24 | 0.15 | 6'30" |
| $S_{2b}$ | 0.38 | 0.34 | 5'18" |
| $S_{3b}$ | 0.59 | 0.51 | 4'49" |
| $S_{4b}$ | 0.66 | 0.40 | 4'47" |
| $S_{5b}$ | 0.50 | 0.58 | 4'54" |
| $S_{6a}$ | 0.42 | 0.22 | 6'18" |
| $S_{6b}$ | 0.50 | 0.40 | 4'42" |
| $S_{7b}$ | 0.44 | 0.25 | 4'54" |
| $S_{8a}$ | 0.56 | 0.40 | 6'24" |
| $S_{8b}$ | 0.70 | 0.54 | 4'48" |
| $S_{9b}$ | 0.56 | 0.48 | 4'52" |
| $S_{10a}$ | 0.43 | 0.24 | 6'20" |
| $S_{10b}$ | 0.61 | 0.39 | 4'47" |
| $S_{11a}$ | 0.27 | 0.16 | — |
| $S_{11b}$ | 0.49 | 0.35 | 4'47" |
| $S_{12b}$ | 0.49 | 0.60 | 4'47" |
| $S_{13b}$ | 0.46 | 0.36 | 5'37" |
| $S_{14a}$ | 0.52 | 0.37 | — |
| $S_{14b}$ | 0.62 | 0.50 | 7'05" |

| Tallysomycin | $\lambda_{max}^{H_2O}$nm ($E_{1cm}^{1\%}$) | Anal. found C | H | N |
|---|---|---|---|---|
| $S_{1a}$ | 242(126), 292(102) | | | |
| $S_{1b}$ | 242(108), 290(94) | 39.54 | 5.45 | 15.01 |
| $S_{2a}$ | 240(120), 290(108) | | | |
| $S_{2b}$ | 244.5(129), 292(104) | 38.51 | 5.51 | 14.30 |
| $S_{3b}$ | 240(123), 291(112) | | | |
| $S_{4b}$ | 242(120), 290(103) | | | |
| $S_{5b}$ | 244(124), 290(102) | 40.17 | 6.05 | 15.02 |
| $S_{6a}$ | 243(105), 291(83) | 39.73 | 6.39 | 15.35 |
| $S_{6b}$ | 243(128), 291(103) | 39.81 | 6.00 | 15.21 |
| $S_{7b}$ | 245(120), 290(96) | 40.89 | 6.04 | 14.51 |
| $S_{8a}$ | 243(107), 291(85) | | | |
| $S_{8b}$ | 243(114), 290(92) | 40.73 | 6.18 | 14.79 |
| $S_{9b}$ | 243(104), 290(87) | 39.80 | 5.97 | 15.42 |
| $S_{10a}$ | 244(142), 292(112) | 39.76 | 5.94 | 15.58 |
| $S_{10b}$ | 244(141), 292(116) | 38.81 | 5.85 | 14.74 |
| $S_{11a}$ | 244(62), 292(53) | | | |
| $S_{11b}$ | 244(112), 292(91) | 40.16 | 5.48 | 15.04 |
| $S_{12b}$ | 245(74), 292(59) | 34.98 | 5.09 | 13.04 |
| $S_{13b}$ | 243(142), 292(114) | 39.14 | 5.85 | 13.63 |
| $S_{14a}$ | 243(102), 292(72) | | | |
| $S_{14b}$ | 243(143), 292(109) | | | |

**TLC system S-102 uses Kiesel gel 60F$_{254}$ (Merck) plate and solvent system of methanol:aqueous 10% ammonium acetate (1:1 v/v); TLC system S-123 uses Kiesel gel 60F$_{254}$ (Merck) plate and solvent system of methanol:10% ammonium acetate:10% ammonium hydroxide (10:9:1 v/v).

Detection was made by Dual-wavelength TLC scanner (Shimadzu GS-910) at 290nm

++Apparatus: Waters Associates Model ALC 204 with a type U6K injector Column: Waters Associates μBondapak $C_{18}$ (4 × 300mm) pre-washed with 0.5% EDTA solution Mobile phase: $CH_3CN:H_2O$ (3:7 v/v) containing Waters Associates reagent PIC B-7

Detector: Model 440uv detector at 254nm

Flow rates: 1.0 ml/min (pressure 800 psi)

Sample size injected: 1 μl of 2 mg/ml solution

This invention is capable of industrial application.

We claim:

1. A tallysomycin A derivatives having the formula

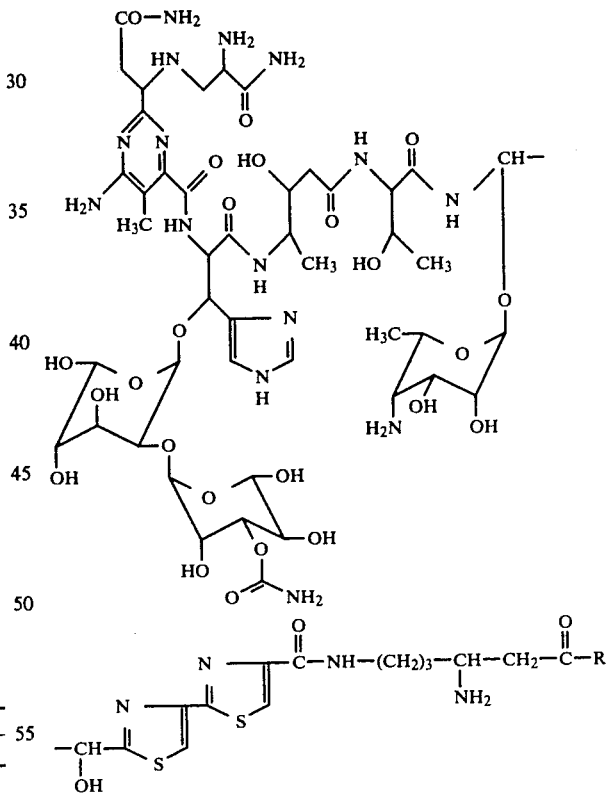

wherein
R is:
—NH—$(CH_2)_3$—$NH_2$
—NH—$(CH_2)_3$—$S^{\oplus}(CH_3)_2$
—NH—$(CH_2)_3$—NH—$CH_2$—$CH_2OH$
—NH—$(CH_2)_3$—$N(CH_2CH_2OH)_2$
—NH—$(CH_2)_4$—$NH_2$
—NH—$(CH_2)_3$—NH—$CH_3$ or

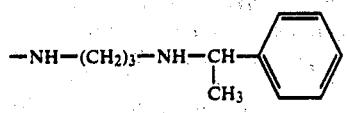

or a pharmaceutically acceptable acid addition salt thereof.

2. The compound of claim 1 named tallysomycin S$_{1a}$ wherein R is —NH—(CH$_2$)$_3$NH$_2$, or a pharmaceutically acceptable acid addition salt thereof.

3. The compound of claim 1 named tallysomycin S$_{2a}$ wherein R is —NH—(CH$_2$)$_3$—S$^{\oplus}$(CH$_3$)$_2$, or a pharmaceutically acceptable acid addition salt thereof.

4. The compound of claim 1 named tallysomycin S$_{6a}$ wherein R is —NH—(CH$_2$)$_3$—NH—CH$_2$CH$_2$OH, or a pharmaceutically acceptable acid addition salt thereof.

5. The compound of claim 1 named tallysomycin S$_{8a}$ wherein R is —NH—(CH$_2$)$_3$—N(CH$_2$CH$_2$OH)$_2$, or a pharmaceutically acceptable acid addition salt thereof.

6. The compound of claim 1 named tallysomycin S$_{10a}$ wherein R is —NH—(CH$_2$)$_4$—NH$_2$, or a pharmaceutically acceptable acid addition salt thereof.

7. The compound of claim 1 named tallysomycin S$_{11a}$ wherein R is —NH—(CH$_2$)$_3$—NH—CH$_3$, or a pharmaceutically acceptable acid addition salt thereof.

8. The compound of claim 1 named tallysomycin S$_{14a}$ wherein R is

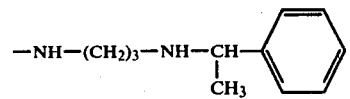

or a pharmaceutically acceptable acid addition salt thereof.

9. A tallysomycin B derivative having the formula

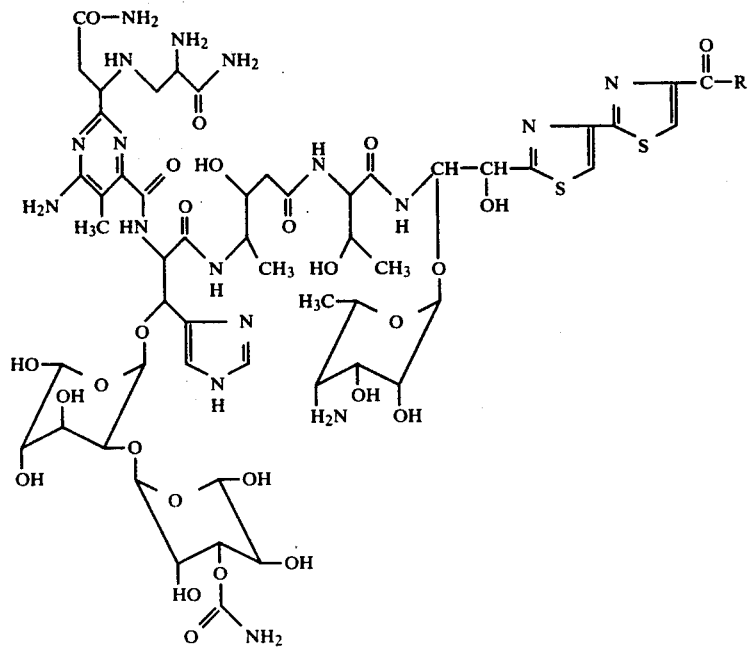

wherein R is:
  —NH—(CH$_2$)$_3$—NH$_2$

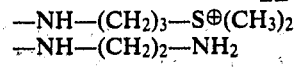
—NH—(CH$_2$)$_3$—S$^{\oplus}$(CH$_3$)$_2$
—NH—(CH$_2$)$_2$—NH$_2$

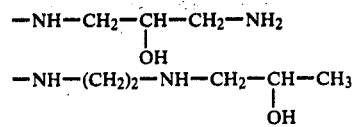
—NH—CH$_2$—CH—CH$_2$—NH$_2$
         |
         OH
—NH—(CH$_2$)$_2$—NH—CH$_2$—CH—CH$_3$
                       |
                       OH —NH—(CH$_2$)$_3$—NH—CH$_2$—CH$_2$OH
—NH—(CH$_2$)$_3$—N(CH$_3$)$_2$
—NH—(CH$_2$)$_3$—N(CH$_2$CH$_2$OH)$_2$
—NH—(CH$_2$)$_2$—NH—CH$_2$—CH$_2$OH
—NH—(CH$_2$)$_4$—NH$_2$
—NH—(CH$_2$)$_3$—NH—CH$_3$

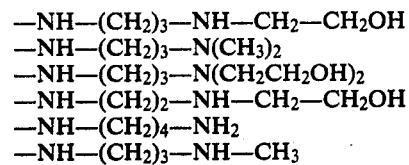

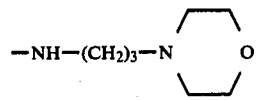

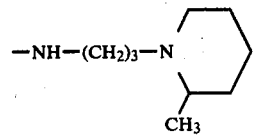

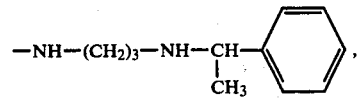

or a pharmaceutically acceptable acid addition salt thereof.

10. The compound of claim 9 named tallysomycin S$_{1b}$ wherein R is —NH—(CH$_2$)$_3$—NH$_2$, or a pharmaceutically acceptable acid addition salt thereof.

11. The compound of claim 9 named tallysomycin S$_{2b}$ wherein R is —NH—(CH$_2$)$_3$—S$^{\oplus}$(CH$_3$)$_2$, or a pharmaceutically acceptable acid addition salt thereof.

12. The compound of claim 9 named tallysomycin S$_{3b}$ wherein R is —NH—(CH$_2$)$_2$—NH$_2$, or a pharmaceutically acceptable acid addition salt thereof.

13. The compound of claim 9 named tallysomycin S$_{4b}$ wherein R is

—NH—CH$_2$—CH(OH)—CH$_2$—NH$_2$, or a pharmaceutically acceptable acid addition salt thereof.

14. The compound of claim 9 named tallysomycin S$_{5b}$ wherein R is

—NH—(CH$_2$)$_2$—NH—CH$_2$—CH(OH)—CH$_3$, or a pharmaceutically acceptable acid addition salt thereof.

15. The compound of claim 9 named tallysomycin S$_{6b}$ wherein R is —NH—(CH$_2$)$_3$—NH—CH$_2$—CH$_2$OH, or a pharmaceutically acceptable acid addition salt thereof.

16. The compound of claim 9 named tallysomycin S$_{7b}$ wherein R is —NH—(CH$_2$)$_3$—N(CH$_3$)$_2$, or a pharmaceutically acceptable acid addition salt thereof.

17. The compound of claim 9 named tallysomycin S$_{8b}$ wherein R is —NH—(CH$_2$)$_3$—N(CH$_2$CH$_2$OH)$_2$, or a pharmaceutically acceptable acid addition salt thereof.

18. The compound of claim 9 named tallysomycin S$_{9b}$ wherein R is —NH—(CH$_2$)$_2$—NH—CH$_2$—CH$_2$OH, or a pharmaceutically acceptable acid addition salt thereof.

19. The compound of claim 9 named tallysomycin S$_{10b}$ wherein R is —NH—(CH$_2$)$_4$—NH$_2$, or a pharmaceutically acceptable acid addition salt thereof.

20. The compound of claim 9 named tallysomycin S$_{11b}$ wherein R is —NH(CH$_2$)$_3$—NH—CH$_3$, or a pharmaceutically acceptable acid addition salt thereof.

21. The compound of claim 9 named tallysomycin S$_{12b}$ wherein R is

—NH—(CH$_2$)$_3$—N$\diagup$O, or a pharmaceutically acceptable acid addition salt thereof.

22. The compound of claim 9 named tallysomycin S$_{13b}$ wherein R is

—NH—(CH$_2$)$_3$—N(piperidinyl-CH$_3$), or a pharmaceutically acceptable acid addition salt thereof.

23. The compound of claim 9 named tallysomycin S$_{14b}$ wherein R is

—NH—(CH$_2$)$_3$—NH—CH(CH$_3$)—C$_6$H$_5$, or a pharmaceutically acceptable acid addition salt thereof.

* * * * *